United States Patent [19]

Islam et al.

[11] Patent Number: 6,159,746

[45] Date of Patent: *Dec. 12, 2000

[54] SOLID PHASE IMMUNOASSAY TO DETECT INHIBITORS OF PROTEOLYTIC ENZYMES

[75] Inventors: Khalid Islam, Como; Lucia Carrano, Uboldo, both of Italy; Maurizio Denaro, Del Mar, Calif.

[73] Assignee: Gruppo Lepetit S.p.A., Milan, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/714,159

[22] PCT Filed: Mar. 9, 1995

[86] PCT No.: PCT/EP95/00867

§ 371 Date: Sep. 23, 1996

§ 102(e) Date: Sep. 23, 1996

[87] PCT Pub. No.: WO95/26505

PCT Pub. Date: Oct. 5, 1995

[30] Foreign Application Priority Data

Mar. 29, 1994 [EP] European Pat. Off. ............... 94104922

[51] Int. Cl.$^7$ .................................................. G01N 33/533
[52] U.S. Cl. ........................... 436/518; 435/7.1; 435/7.9; 435/7.92; 435/7.95; 436/532; 436/815; 530/810; 530/811; 530/816; 530/839
[58] Field of Search .................. 435/7.1, 7.9, 7.92–7.95; 436/518, 532, 815, 810; 530/811, 816, 839

[56] References Cited

U.S. PATENT DOCUMENTS

| | | |
|---|---|---|
| 5,171,662 | 12/1992 | Sharma . |
| 5,288,612 | 2/1994 | Griffin et al. ............................ 435/23 |
| 5,492,812 | 2/1996 | Vooheis .................................. 435/7.1 |

FOREIGN PATENT DOCUMENTS

| | | |
|---|---|---|
| 0518557 | 12/1992 | European Pat. Off. . |
| 0564946 | 10/1993 | European Pat. Off. . |
| 9207068 | 4/1992 | WIPO . |

OTHER PUBLICATIONS

Corces et al., European Journia of Biochemistry, 105:7–16, 1980.
Furtner et al., European Journal of Cell Biology, 45:1–8, 1987.
Hammarback et al., The Journla of Biological Chemistry, 265:22:12763–12766, 1990.
Herrmann et al., The Journla of Biological Chemistry, 262:3:1320–1325, 1987.
Kuriyama R., Journal of Cell Science, 66:277–293, 1984.
Leterrier et al., Journal of Neurochemistry, 43:5:1385–1391, 1984.
Brugg et al., The Journal of Cell Biology, 114:4:735–743, 1991.
Obar et al., Neuron, 3:639–645, 1989.
Pedrotti et al., Biochemistry, 33:8798–8806, 1994.
Serrano et al., Methods in Enzymology, 134:179–190, 1986.
Wiche et al., Experimental Cell Research, 138:15–29, 1982.
Zauner et al., European Journal of Cell Biology, 57:66–74, 1992.
Asai et al., Cell Motility, 2:599–614 (1982), "Two different monoclonal antibodies to alph–tublin . . . ".
Elliott et al., Molecular and Cellular Biology, 6(3):906–913 (1986), "Complete sequence of thre alfa–tublin . . .".

*Primary Examiner*—Christopher L. Chin
*Assistant Examiner*—Bao-Thuy L. Nguyen
*Attorney, Agent, or Firm*—Ruth E. Homan

[57] ABSTRACT

Solid phase immunoassay for detecting specific inhibitors of proteolytic enzymes in biological fluids, which comprises: a) contacting a tubulin peptide covalently linked to a support with a solution containing a proteolytic activity together with a protease inhibitor, b) detecting the inhibitor activity against the selected proteases by contacting the support with a solution containing a labelled monoclonal antibody which specifically recognises the free end of the tubulin peptide linked to the support.

6 Claims, No Drawings

SOLID PHASE IMMUNOASSAY TO DETECT INHIBITORS OF PROTEOLYTIC ENZYMES

The present invention refers to a solid phase immunoassay for detecting specific inhibitors of proteolytic enzymes in biological fluids or in any kind of solution containing them, as well as for detecting proteolytic activities in any solution containing them.

At present, a number of methods for assay of protease and anti-proteolytic activity on protein substrate are available. Among the known methods, the assays in which proteases and their inhibitors are determined by using mono- or polyclonal antibodies are the most specific and sensitive. However, no one of such procedures is universally suitable given the diversity and specificity of the proteases, thus requiring different methods for different classes of proteases.

The assay of the invention comprises contacting a tubulin protein or a tubulin-like peptide covalently linked to a suitable support with a solution containing a proteases together with a related inhibitor and determining said inhibitor by using a monoclonal antibody which specifically recognizes the free end of the linked tubulin. Within the meaning of the term "tubulin-like peptide" is comprised any peptide on which the more common classes of proteases are active and the free end of which is identical to the free end of tubulin. With the term "free end", it is intended the end of the tubulin protein or of the peptide which is not linked to the support; as said protein or peptide are linked to the support preferably via their N-terminus, in general the "free end" corresponds to the C-terminus end of the amino acid sequence.

With the present assay it is possible to determine the inhibitors of the more common classes of proteases at the same time, using the same peptidic substrate and the same detection antibody.

The method of the present invention may also be employed to detect the presence of the above proteases in the tested solution, by detecting them with specific known inhibitors.

With the present assay it is also possible to compare the inhibition potency of a given inhibitor which is normally obtained in admixture with unknown substances, thus permitting to follow the purification of said inhibitor.

The method of the invention is accurate, precise, rapid and easy to practice. The intra- and inter- assay precision are well within the range of values currently accepted for analytical purposes.

With the assay of the present invention, the activity of the inhibitors can also be determined when any impurity is present in the tested solution, as after the enzymatic reaction the peptidic substrate is thoroughly washed before detecting the activity of the inhibitor.

Another object of the present invention is a kit for use in the above method for determining anti-proteolytic activities, which comprises a support to which a tubulin protein or a tubulin-like peptide is covalently linked and a solution containing a monoclonal antibody which specifically recognizes the free end of the linked tubulin.

Preferred proteases for which the method of the present invention is particularly useful are the proteases of the serine, aspartic and cysteine classes.

As mentioned above, the peptidic substrate which is employed in the assay of the present invention for determining the inhibition of anti-proteolytic substances against the above proteases is tubulin or a tubulin-like peptide. Preferably, animal tubulin is employed, particularly preferred being bovine brain tubulin.

Such a protein is obtained by means of purification and separation procedures known in the art. For instance, bovine brain tubulin may be purified from bovine brain extract according to Islam K. and R. G. Burns, FEBS Lett., 123, 1981, pp. 181–185 and R. G. Burns and Islam K., Europ. Jour. Biochem., 117, 1981, 515–519; separation of tubulin from microtubule-associated proteins (MAPs) may be performed by known chromatographic procedures, preferably by ion-exchange chromatography according to Vallee et al. in "Methods in Enzymology", 134, 1986, pp. 89–116.

In general, tubulin is obtained, and employed in the present assay, as an equimolar mixture of α- and β-tubulin. Both these protein have suitable digestion sites for the more common classes of proteases, but they differ for the amino acid sequence of the C-terminus end of the protein. The consequence is that the specific monoclonal antibody used for detecting the undigested protein, preferably a monoclonal antibody which specifically recognizes the C-terminus of α-tubulin, will recognize only one of the two undigested tubulin proteins; this difference is however of no practical relevance for the results of the assay of the present invention, because of the constant equimolarity of the α- and β-tubulin mixture employed.

As it readily appears to the skilled man not only tubulin but also any degradation product of tubulin or any modified tubulin may be employed for the immunoassay of the present invention, insofar as said peptide has suitable digestion sites for the more common classes of proteases, while maintaining the characteristic C-terminus end of tubulin, preferably α-tubulin.

As mentioned above, any peptide on which the more common classes of proteases are active and the C-terminus end of which is identical to the C-terminus end of tubulin, preferably α-tubulin, may also be employed.

Said peptide shall therefore contain the characteristic digestion sites for the detected proteases. For instance, peptides containing Leu, Phe or Tyr may be digested by Elastase or Chymotrypsin (Serine proteases); peptides containing Phe or Tyr may be digested by Pepsin and Cathepsin D (Aspartic proteases); peptides containing Arg or Lys may be digested by Trypsin (Serine protease); peptides containing the sequence Tyr-Pro-Leu may be digested by Renin (Aspartic protease); peptides containing Phe may be digested by Cathepsin B (Cysteine protease); peptides containing Arg, His or Gly may be digested by Papain (Cysteine protease).

The specific amino acid sequence of the C-terminus end of the peptide will depend upon the monoclonal antibody employed for detecting the undigested peptide. For instance, when YL ½ antibody is employed, the amino acid sequence of the C-terminus end of the peptide will be: -Glu-Gly-Glu-Gly-Glu-Glu-Glu-Gly-Glu-Glu-Tyr. This sequence corresponds to the sequence of 11 amino acids of the C-terminus end of α-tubulin.

As tubulin-like peptides, synthetic peptides may be employed. Conveniently, a new synthetic peptide consisting of 21 amino acids is employed, wherein the last 11 amino acids of the C-terminus end of said peptide are identical to those of the C-terminus end of tubulin.

The amino acid sequence of said novel peptide (SEQ ID NO: 1) is:

Phe-His-Arg-Leu-Tyr-Pro-Leu-Gly-Pro-Val-Glu-Gly-Glu-Gly-Glu-Glu-Glu-Gly-Glu-Glu-Tyr

Natural amino acids, with the exception of glycine, contain a chiral atom of carbon. For the scope of the present invention, the amino acids of the above peptide are meant to be in their L-configuration.

The peptide of this invention can be prepared by a variety of procedures readily known to those skilled in the art. Such procedures include the solid phase sequential procedure, according to the method of Merrifield, which can be performed using established automated methods such as by use of an automated peptide synthesizer.

The resin support employed can be any suitable resin conventionally employed in the art for the solid phase preparation of polypeptides, preferably polystyrene which has been cross-linked with from 0.5 to about 3 percent divinyl benzene, which has been either converted to the p-methylbenzhydrylamine or benzhydrylamine derivative (for C-terminal amides) or chloromethylated or hydroxymethylated to provide sites for ester formation with the initially introduced α-amino protected amino acid (for producing C-terminal alkylamides) and esters.

An example of hydroxymethyl resin is described by Bodanszky, et al., *Chem. Ind.* (London) 38, 1597–98 (1966), while the protected amino acid can be bound to the resin according to Gisin, *Helv. Chem. Acta*, 56 1476 (1973). Examples and preparation of such modified poly-styrene resins are described by J. M. Stewart et al., "Solid Phase Peptide Synthesis" (Pierce Chem. Co., Rockford, Ill.) 1984, pp. 53–60. Many resin and resin bound protected amino acids are commercially available, e.g. the chloromethylated resin from Bio Rad Laboratories (Richmond, Calif.). For instance, to prepare the polypeptide of this invention wherein the C-terminus is a Tyr residue, a 2-bromobenzyloxycarbonyl (2-BrZ) protected Tyr bound to a benzylated, hydroxy-methylated phenylacetamidomethyl resin can be used and is commercially available (e.g. ABI APPLIED BIOSYSTEM®).

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of from 0° C. to room temperature. Other standard cleaving reagents and conditions for removal of specific α-amino protecting groups may be used. After removal of the α-amino protecting group the other amino protected amino acids are coupled step-wise in the desired order.

Alternatively, multiple amino acid groups may be coupled by the solution method prior to coupling with the resin supported amino acid sequence.

The α-amino protecting group employed with each amino acid introduced into the polypeptide sequence may be any such protecting group known to the art.

Among the classes of α-amino protecting groups contemplated are (1) acyl type protecting groups such as: formyl, trifluoroacetyl, phthalyl, toluenesulfonyl (tosyl), benzenesulfonyl, nitro-phenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzylcarbonyl, p-bromobenzyloxycarbonyl, p-methoxybenzyloxycarbonyl, 1-(p-biphenylyl)-1-methylethoxycarbonyl, α,α-dimethyl-3,5-dimethoxybenzyloxycarbonyl and benzhydryloxycarbonyl and 9-fluorenylmethoxycarbonyl (Fmoc); (3) aliphatic urethan protecting groups such as tert-butyloxycarbonyl (Boc), diisopropylmethoxycarbonyl, isopropyloxycarbonyl, ethoxycarbonyl and allyloxy-carbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tertbutyloxycarbonyl.

The selection of an appropriate coupling reagent is within the skill of the art. Illustrative examples are (1) carbodiimides (e.g., N,N'-dicyclohexylcarbodiimide (DCC) and N-ethyl-N'-(γ-dimethylaminopropylcarbodiimide); (2) cyanamides (e:g:, N,N-dibenzylcyanamide); (3) ketenimines; (4) isoxazolium salts (e:g:, N-ethyl-%-phenylisoxazolium-3'-sulfonate; (5) monocyclic nitrogen containing heterocyclic amides of aromatic character containing one through four nitrogens in the ring such as imidazolides, pyrazolides, and 1,2,4-triazolides; specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., (Boc-Ala)$_2$-O) and (8) nitrogen containing heterocyclic compounds having a hydroxy group on one ring nitrogen (e.g., N-hydroxyphthalimide, N-hydroxysuccinimide and 1-hydroxybenzotriazole (HOBT)). Other activating reagents and their use in peptide coupling are described by Kapoor, *J. Pharm. Sci.*, 59, pp. 1–27 (1970). For the synthesis of the peptide of the present invention, applicant prefer the use of DCC/HOBT, in N-methylpyrrolidinone (NMP), as coupling reagent.

Each protected amino acid or amino acid sequence is introduced into the solid phase reactor in about a fourfolder excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al., *Analyt. Biochem.* 34, 595 (1970).

After the desired amino acid sequence has been obtained, the peptide is removed from the resin. The whole protected peptide is released either from the chloromethylated resin by ammoniolysis to obtain the protected amide, or by hydrofluoric acid to obtain the acid, or from the methylbenzhydrylamine or benzhydrylamine resins by treatment with a solution of dimethyl sulfide, p-cresol or thiocresol in liquid hydrofluoric acid, at a temperature of about 0° C.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed during cleavage of the protecting group of the α-amino moiety. For example, suitable side chain protecting groups for tyrosine are 2-halo-benzyloxycarbonyl derivatives, such as $^2$-bromobenzyloxycarbonyl (2-BrZ), the carboxylic group of glutamic acid can be protected with a benzyl (Bzl) or cyclohexyl ester (Chx) group, histidine is conveniently protected with a benzyloxymethyl (Bom) or a tosile group (Tos), while the tosile group (Tos) is also suitable for protecting the side chain of arginine.

These groups can be removed by procedures well known in the art. Typically protecting group removal is done after the peptide chain synthesis is complete, as the condition for removing the peptide from the resin are in general also suitable for removing the protecting groups of the side chains. However, the protecting groups can be removed at any other appropriate time.

After the peptide has been removed from the resin and deprotected, it is purified according to known chromatographic techniques, preferably by HPLC, thus obtaining the desired pure peptide.

The method for carrying out the immunoassay of the present invention comprises:
  a) contacting a tubulin protein or a tubulin-like peptide covalently linked to a suitable support with a solution containing a proteolytic activity together with a protease inhibitor (which may be either a known compound or an activity to be investigated);
  b) detecting the inhibitor activity against the selected proteases by contacting the support with a solution containing a labelled monoclonal antibody which specifically recognises the free end of the tubulin protein linked to the support.

The support to which the tubulin protein or the tubulin-like peptide is linked is any analytical support to which the protein or peptide may covalently be linked, preferably via its N-terminus. Examples of analytical supports which may be employed are glass or plastic microtiter plates or test tubes, plastic sheets, nitrocellulose and nylon membranes. The most preferred analytical support is represented by the wells of microtiter plates made of polymeric materials, such as polyethylene, polystyrene, or polyvinylchloride. Such polymers of the microtiter plates wells may either contain functional groups able to covalently link tubulin or tubulin-like peptide, or preferably they may be activated by linking to the support a so-called "spacer arm" containing a functional group which activates the support's surface, thus allowing the linkage of the protein, preferably via the N-terminus. Examples of activating agents are carbodiimide derivatives, N-hydroxysuccynimide derivatives, e.g. N-cyclohexyl-N'-2-4'-methylmorpholynimide, sulfosuccynimide derivatives, e.g. bis(sulfosuccinidimyl)suberate. Preferably, bis(sulfosuccinidimyl)suberate is employed as activating agent.

When the support is duly activated, a buffered solution containing tubulin or a tubulin-like peptide, preferably from 0.001 mg/ml to 0.010 mg/ml, is contacted with said support, preferably for from 1 to 2 hours at a temperature of from 18° C. to 30° C. After washing out the peptidic solution, the possibly unreacted activated groups on the support are saturated by adding an excess of a non-interfering aminoacid solution, such as a buffered solution from 3% to 8% of glycine for 1 to 3 hours.

The term "solution containing a proteolytic activity" is intended to encompass any kind of solution containing a proteolytic activity such as fermentation broths of microorganisms, cells and microorganisms culture media, human biological fluids like plasma, urines, exudates, etc., as well as any analytical solution containing said proteases.

Preferred proteases of which inhibitors may be determined according to the assay of the present invention are: serine proteases such as trypsin, subtilisin, elastase and cathepsin G; aspartic proteases such as pepsin, cathepsin D, renin and Hiv-1 protease; cysteine proteases such as papain and cathepsin B.

The protease inhibitor tested on the selected proteolytic solution may be either a compound with a known inhibitory activity (in this case a calibration curve is obtained, concentration vs. percentage of inhibition) or an unknown substance. In the latter case, it is possible to determine the inhibition activity of the investigated compound by reference with the activity of known inhibitors; furthermore, if the unknown inhibitor has been obtained in admixture with impurities, it is also possible to follow the purification of the active substance by repeating the assay at the different steps of the purification, thus observing an increase in the inhibition activity depending on the higher degree of purity of the compound.

With the term "labelled monoclonal antibody" it is intended a labelled antibody which specifically recognises the free-end of the linked tubulin as well as a system which comprises an antibody and a labelled anti-antibody, wherein the first antibody specifically recognises the free-end of the linked tubulin, while the labelled anti-antibody is specific for the first antibody; in general, a specie specific labelled anti-antibody is conveniently employed. In both cases, antibodies which specifically recognise the C-terminus end of α-tubulin are preferably employed.

The labelling of the antibody is made according to known per se techniques, such as radiolabelling, fluorescence-labelling, enzyme labelling and the like; preferably, enzyme labelling is employed, for instance by linking a peroxidase enzyme to the antibody.

When enzyme labelling is employed, the labelled antibody linked to the supported tubulin is detected by adding a substrate which is specific for the labelling enzyme. The substrate is such that the enzyme transforms said substrate in a compound with different physico-chemical characteristics, which are detectable by means of known analytical techniques. Typically, when the antibody is labelled with a peroxidase enzyme, suitable substrates are solution containing compounds which determine a change in colour of the solution due to the enzymatic reaction, such as o-phenylenediamine or tetramethylbenzidine dihydrochloride; the intensity of the colour of the solution is determined by means of known fotometric techniques, such as colorimetry, spectrofotometry and the like.

As mentioned above, the first step of the present assay is the contact of the supported tubulin or tubulin-like peptide with a solution containing a proteolytic activity as above described. By contacting solutions containing different proteolytic activities and a same inhibitor substance, it is possible to determine both the specificity of said inhibitor against the selected protease and the percentage of inhibition.

The proteolytic solution contains in general from 0.005 to 50 μg/ml of the selected protease, preferably from 0.02 to 5 μg/ml, while the concentration of the inhibitor substance obviously varies according to the specific inhibition power of the substance, or may also be undetermined when an unknown inhibitor is investigated. Optionally, before contacting it with the supported tubulin or tubulin-like peptide, the protease may be pre-incubated together with the anti-proteolytic activity for a determined time at room temperature.

The incubation time of the proteolytic solution with the supported tubulin or tubulin-like peptide ranges from 1 to 5 hours, and is inversely proportional to the incubation temperature which is from 20° C. to 40° C.

After washing the support with a buffered solution, the anti-proteolitic activity, if any, is determined. As said above, detection is carried out by using a labelled monoclonal antibody which specifically recognises the free end of the tubulin protein linked to the support.

Preferably, the detection of the anti-proteolytic activity is performed by using: a) a monoclonal antibody which specifically recognises the C-terminus end of the tubulin protein; b) an enzyme labelled anti-antibody, specific for the above antibody; c) a substrate specific for the above labelling enzyme.

According to a preferred embodiment of the invention, when tubulin or tubulin-like peptide is linked to the support via the N-terminus, the detection of the anti-proteolytic activity is carried out by contacting the immobilized peptide with a solution containing a monoclonal antibody which specifically recognises the C-terminus of the α-tubulin protein, preferably a monoclonal rat antibody (e.g YL ½, Amersham); afterwards, a solution is added containing an enzyme labelled antibody which is specie specific for the first antibody, preferably a secondary peroxidated anti rat antibody when a monoclonal rat antibody has been employed in the previous step.

The immobilizied system tubulin—antibody—labelled antibody is then washed with a buffered solution and treated with a solution containing a specific substrate for the enzyme. Preferably, a substrate which determines a change in colour of the solution as a consequence of the enzymatic reaction is employed, such as o-phenylenediamine or tetramethyl-benzidine dihydrochloride; as the intensity of the colour is proportional to the percentage of inhibition, it is possible to calculate a calibration curve by using known inhibitor solutions, thus determining the inhibition activity of unknown inhibitors. Furthermore it is possible to compare the different inhibition activity of a known inhibitor with respect to the different proteases.

The accuracy of the assay of the present invention is supported by the confirmation of the inhibition data of various known inhibitor substances.

For instance, with the assay of the present invention it is confirmed that pepstatin is a specific inhibitor for the proteases of the aspartic class, with different inhibition constants for the different aspartic proteases. Actually, under the test conditions, the 50% inhibition of cathepsin D and pepsin is obtained with a concentration of about 20 nM of pepstatin, 50% inhibition of renin is obtained with a concentration of about 200 nM of pepstatin, while a concentration of about 2 $\mu$M is necessary to inhibit the Hiv-1 protease at 50%.

Furthermore, with the present assay, it is confirmed the specific inhibition of α-anti trypsin for the proteases of the serine class and the specific inhibition of leupeptin for the proteases of the cysteine class.

The test of the present invention allows also to confirm that the microbial alkaline inhibitor (MAPI) is able to inhibit a number of enzyme of the various proteases classes, according to the data reported in literature (see for instance Watabe and Murao, Agric. Biol. Chem., 1979, 43–250).

As stated above, a further object of the present invention is an analytical kit for use in the method of the present invention. Said kit comprises an analytical support bearing onto its surface a covalently linked tubulin protein or a tubulin-like peptide and a solution containing a labelled monoclonal antibody which specifically recognises the free end of the tubulin protein linked to the support.

The preferred support to which the tubulin or tubulin-like peptide is linked, the preferred way as to covalently link the tubulin or tubulin-like peptide to the support and the preferred labelled monoclonal antibody to be used for the detection of the inhibitor activity are those previously disclosed in the present application.

The present invention will be illustrated more in detail by the following examples.

EXAMPLE 1

Purification of tubulin

Microtubule protein is purified from calf brain through two cycles of temperature-dependent assembly and disassembly according to Islam K. and R. G. Burns, FEBS Lett., 123, 1981, pp. 181–185.

Tubulin is separated from MAPs by applying the above purified protein on the top of a DEAE-Sephadex A-50 column (Pharmacia); the column is washed with PEM buffer solution containing 0.3M NaCl (to elute MAPs) prior to eluting with PEM buffer containing 0.50M NaCl and 0.1 mM guanosine 5-tri-phosphate, according to the procedure described by Vallee et al. in "Methods in Enzymology", 134, 1986, pp. 89–116.

PEM buffer=1.1 1 of PIPES (piperazine-N,N'-bis(2-ethansulphonic acid)-NaOH, pH 6.6, containing 1 mM of EGTA (ethylene glycol bis-(B-aminoethylether)-N,N,N',N'-tetraacetic acid) and 1 mg of $MgSO_4$.

EXAMPLE 1a

Preparation of the peptide Phe-Hys-Arg-Leu-Tyr-Pro-Leu-Gly-Pro-Val-Glu-Gly-Glu-Gly-Glu-Glu-Glu-Gly-Glu-Glu-Tyr The title peptide is synthesized by conventional solid-phase methods using an ABI APPLIED BIOSYSTEMS® Model 430-A Peptide Synthesizer and protocols supplied by the manufacturer. The synthesis is carried out using a Boc-Tyr-(2-BrZ) resin (0.61 mmol/g, 0,5 mmol) and N-Boc amino acids with the following side chains protecting groups: Arg(Tos), His(Bom), Tyr(2-BrZ), Glu(Bzl).

Sequencial coupling is performed using the standard Boc-peptide synthesis control, with DCC/HOBT in NMP. Boc-deprotection at each step is carried out with TFA.

The peptide is cleaved from the resin support and the side chains deprotected with anhydrous hydrogen fluoride/anisole (10:1) at 0° C. After removal of the HF the crude peptide is extracted from the resin with 30% acetic acid and lyophilized.

The peptidic material that remained is purified reverse phase HPLC (Vydac C-18, 22×250 mm) using a Water Deltaprep 3000 system, yielding 91 mg of pure peptide.

The peptide is characterized by analytical HPLC (Vydac 218TP54), FAB Mass Spectrometry and amino acid analysis:

Peptide content (HPLC): 79.0%;

FAB-MS: 2437.2 $(M+H)^+$;

AAA: Glu 6,93 (7), Pro 2,04 (2), Gly 4,10 (4), Leu 2,05 (2), Val 0,94 (1), Tyr 2,01 (2), Phe 0,97 (1), His 0,96 (1), Arg 0,98 (1).

EXAMPLE 2

Covalent linkage of tubulin to the support 0.150 ml of a freshly made phosfate buffered saline (PBS) solution (pH=7.3) containing 0.03 mg of bis(sulfo-succinidimyl)suberate (BS3, Pierce, Rockford, Ill.) are dispensed into each well of a cova-link 96 wells plate (Nunc). The solution is left in the wells at room temperature for 90 minutes, afterwards the wells are washed three times with PBS solution.

Afterwards, 0,150 ml of a PBS solution containing 5% glycine (v/v) and 0.75 $\mu$g of tubulin obtained according to Example 1 is added to each well. After 90 minutes at room temperature, the solution is removed and 0.3 ml of a 5% glycine PBS solution are added. After about 2 hours, the wells are washed with fresh PBS solution.

EXAMPLE 2a

Covalent linkage of the peptide prepared according to example 1a to the support

The covalent linkage of the peptide prepared according to example 1a to the support is obtained by following the procedure according to example 2, but using the peptide obtained according to example 1a instead of tubulin.

EXAMPLE 3

Determination of the anti-proteolytic activity 0.15 ml of a solution containing a proteolytic activity and a known inhibitor (concentration from 0.01 to 10 μg/ml) are added to the wells treated according to Example 2 or Example 2a and incubated for 2 hours at 37° C.

The employed proteolytic enzymes are:

Serine class: trypsin (0.25 μg/ml), subtilisin (0.25 μg/ml), elastase (0.5 μg/ml) and cathepsin G (5 μg/ml), in a 20 mM solution of Tris-hydroxymethyl-aminomethanchloride (TRIS) (pH=7.4);

Aspartic class: pepsin (5 μg/ml), cathepsin D (5 μg/ml), renin (5 μg/ml) and Hiv-1 protease (5 μg/ml), in a 50 mM acetate buffer solution (pH=5.5) containing 0.01% Tween 20 (Pierce);

Cysteine class: papain (0.25 μg/ml) and cathepsin B (10 μg/ml) in a 50 mM acetate buffer solution (pH=5.5) containing 5 mM cysteine.

The inhibitors tested are pepstatin (inhibitor of aspartic class), α-anti trypsin (inhibitor of the serine class), leupeptin (inhibitor of the cysteine class) and MAPI (non-specific inhibitor). Table I reports the concentration of these inhibitors which determines a 50% inhibition of the above proteases.

After three rapid washing with PBS solution (pH=7.3), the inhibitory activity is determined as follows:

A YL ½ antibody solution (Amersham) diluted 1:1000 in PBS buffer is added to each well and incubated for 1 hour at room temperature. After three rapid washing with PBS solution, an anti-rat peroxydated antibody solution (Amersham) diluted 1:1000 in PBS buffer is added to each well and incubated for 1 hour at room temperature. After 10–15 minutes, the colour is developed with a 0.5 M citric acid solution (pH=5.5) containing 1 mg/ml of o-phenylendiamine. After 5–10 minutes, the reaction is stopped with $H_2SO_4$ 4 M. The colour is detected on a Titertek Multiscan MCC340-HK spectrophotometer reading the absorbance at 492 nm. The results are reported in the following table I.

TABLE I

Concentration of inhibitor in the proteolytic solution which determines the 50% inhibition of the protease

| Proteases | Conc. (μg/ml) | Pepstatin | α-anti trypsin | Leupeptin | MAPI |
|---|---|---|---|---|---|
| Trypsin | 0.25 | n.i. | 1.0 | n.i. | 2.5 |
| Subtilisin | 0.25 | n.i. | 7.5 | n.i. | 4.0 |
| Elastase | 0.5 | n.i. | 1.0 | n.i. | n.i. |
| Cathepsin G | 5 | n.i. | n.i. | n.i. | n.i. |
| Pepsin | 5 | 0.03 | n.i. | n.i. | 10 |
| Cathepsin D | 5 | 0.03 | n.i. | n.i. | 10 |
| Renin | 5 | 0.3 | n.i. | n.i. | n.i. |
| Hiv-1 protease | 5 | 3 | n.i. | n.i. | n.i. |
| Papain | 0.25 | n.i. | n.i. | 0.05 | 0.08 |
| Cathepsin B | 10 | n.i. | n.i. | 2.5 | 0.6 | n.i. = no inhibition

EXAMPLE 5

Example 3 is repeated, but the proteolytic solution is pre-incubated with the inhibitor at room temperature for 5 minutes. The same results as in Example 3 are obtained.

EXAMPLE 6

Example 3 is repeated, but the solution containing the proteolytic activity and the known inhibitor is incubated for about 3½ hours at 25° C. on the supported tubulin. The same results as in Example 3 are obtained.

What is claimed is:

1. A method for detecting protease inhibiting activity of an inventigational compound comprising contacting a peptide substrate having an N-terminus and a C-terminus, wherein the N-terminus is linked to a solid support phase, with a protease, in the presence of the inventigational compound, and detecting inhibitor activity of the investigational compound b determining whether the peptide substrate is cleaved by adding a labeled monoclonal antibody that binds the C-terminal end of the peptidic substrate, wherein the peptidic substrate is a peptide having a C terminus amino acid sequence of Phe-His-Arg-Leu-Tyr-Pro-Leu-Gly-Pro-Val-Glu-Gly-Glu-Gly-Glu-Glu-Glu-Gly-Glu-Glu-Tyr.

2. The method according to claim 1 wherein the solid support phase is a polymer which is selected from the group consisting of polyethylene, polystyrene, and polyvinylchloride, and the peptidic substrate is linked to the support by means of an activating agent selected from carbodimide derivatives, N-hydroxysuccynimide derivatives and sulfosuccynimide derivatives.

3. The method according to claim 1 wherein the label is a peroxidase enzyme.

4. The method according to claim 2 wherein the activating agent is bis(sulfosuccinidimyl)suberate.

5. An analytical kit which comprises: a support bearing on its surface a peptidic substrate, which substrate has an N-terminus which is covalently linked to the support and a C-terminus, wherein the substrate is a peptide having a C-terminus amino acid sequence of Phe-His-Arg-Leu-Tyr-Pro-Leu-Gly-Pro-Val-Glu-Gly-Glu-Gly-Glu-Glu-Gly-Glu-Glu-Tyr, and a solution containing a labeled monoclonal antibody which specifically binds the C-terminus of the substrate.

6. A synethic peptide having the following amino acid sequence, SEQ ID. No. 1:

Phe-His-Arg-Leu-Tyr-Pro-Leu-Gly-Pro-Val-Glu-Gly-Glu-Gly-Glu-Glu-Glu-Gly-Glu-Glu-Tyr.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Source: Completely synthesized

<400> SEQUENCE: 1

Phe His Arg Leu Tyr Pro Leu Gly Pro Val Glu Gly Glu Gly Glu Gly
 1               5                  10                  15

Gly Glu Gly Gly Tyr
            20